United States Patent [19]
Marx et al.

[11] Patent Number: 6,150,505
[45] Date of Patent: Nov. 21, 2000

[54] FIBRIN MICROBEADS PREPARED FROM FIBRINOGEN, THROMBIN AND FACTOR XIII

[75] Inventors: Gerard Marx, New York, N.Y.; Raphael Gorodetsky, Malha, Israel

[73] Assignee: Hadasit Medical Research Services & Development Ltd., Jerusalem, Israel

[21] Appl. No.: 08/934,283

[22] Filed: Sep. 19, 1997

[51] Int. Cl.$^7$ .......................... A61K 35/14; C12N 11/02; C12N 5/00; C07K 14/00

[52] U.S. Cl. ......................... 530/382; 424/409; 424/489; 435/177; 435/182; 435/395; 530/383; 530/402

[58] Field of Search ................... 435/212, 180, 435/177, 182, 395; 530/382, 383, 402; 424/490, 491, 499, 450, 468, 469, 409, 489

[56] References Cited

U.S. PATENT DOCUMENTS

| | | | |
|---|---|---|---|
| 3,663,687 | 5/1972 | Evans | 424/1.25 |
| 3,937,668 | 2/1976 | Zolle | 424/1.29 |
| 4,147,767 | 4/1979 | Yapel, Jr. | 424/499 |
| 5,069,936 | 12/1991 | Yen | 427/213.33 |
| 5,260,420 | 11/1993 | Burnouf-Fadosevich et al. | 530/382 |
| 5,324,647 | 6/1994 | Rubens et al. | 435/180 |
| 5,635,609 | 6/1997 | Levy et al. | 536/2 |
| 5,783,214 | 7/1998 | Royer | 424/499 |

FOREIGN PATENT DOCUMENTS

| | | |
|---|---|---|
| 05292899 | 11/1993 | Japan . |
| 9404261 | 8/1993 | WIPO . |
| 9404260 | 3/1994 | WIPO . |

OTHER PUBLICATIONS

Ho et al. "Fibrin–based drug delivery systems. II. The preparation and characterization of microbeads," Drug Develop. Industrial Pharm. (1994) 20(4): 535–546, 1994.

Ho et al. "Fibrin–based delivery systems III: The evaluation of the release of macromolecules from microbeads," J. Controlled Release (1995) 34: 65–70, 1995.

Miyazaki et al. "Fibrinogen microspheres as novel drug delivery systems for antitumor drugs," Chem. Pharm. Bull. (1986) 34(3): 1370–75, 1986.

Dickinson et al. "Rheology of milk protein gels and protein–stabilized emulsion gels cross–linked with trans-glutaminase," J. Agric. Good Chem. (1996) 44: 1371–1377, 1996.

Lee, et al. Serum Albumin Beads: An Injectable, Biodegradable System for the Sustained Release of Drugs, *Science* 213:233–235 (1981).

Miyazaki, et al., Preparation and evaulation in Vitro and in Vivo of Fibrinogen Microspheres Containing Adriamycin, *Chem. Pharm. Bull.* (Tokyo), 1986, 34(8): 3384–93.

Arshady, R., Microspheres and Microcapsules: A Survey of Manufacturing Techniques, Part I: Suspension Cross–Linking, *Polymer Engineering And Science 29* (24): 1746–1758, 1989.

Arshady, R., Microspheres and Microcapsules: A Survey of Manufacturing Techniques. Part II: Coacervation, *Polymer Engineering And Science*, 30 (15): 905–914, 1990.

Arshady, R., Microspheres and Microcapsules: A Survey of Manufacturing Techniques: Part III: Solvent Evaporation, *Polymer Engineering And Science*, 30 (15): 915–924, 1990.

Suslick, et al., Protein Microencapsulation of Non–Aqueous Liquids, *Journal of American Chemical Society 112*:7807–7809, 1990.

Yapel, Albumin Microspheres: Heat and Chemical Stabilization, *Methods in Enzymology 112*:3–43 (1985).

Elisha Berman, et al., "An early transient increase of intracellular Na$^+$may be one of the first components of the mitogenic signal. Direct detection by$^{23}$Na–NMR spectroscopy in quiescent 3T3 mouse fibroblasts stimulated by growth factors." Biochimica et Biophysica Acta 1239, (1995), 177–185.

Richard I. Senderoff, et al., "Fibrin Based Drug Delivery Systems. Journal of Parenteral Science and Technology", vol. 45, No. 1, Jan./Feb., 1991.

*Primary Examiner*—David M. Naff
*Assistant Examiner*—Michael V. Meller
*Attorney, Agent, or Firm*—Amster, Rothstein & Ebenstein

[57] ABSTRACT

The present invention provides fibrin microbeads that are biologically active and comprise extensively cross-linked fibrin(ogen) without using glutaraldehyde, and a method for preparing the fibrin microbeads. The present invention also provides a composition comprising cells bound to the fibrin microbeads, and methods for culturing and separating cells using the fibrin microbeads of the present invention. Finally, the present invention provides methods for transplanting cells and engineering tissue using the fibrin microbeads of the present invention.

16 Claims, 10 Drawing Sheets

SEM of fibrin microbeads (FMB) with cultured cells.

FMB + Fibroblasts

FIBRIN MICROBEADS PREPARED FROM FIBRINOGEN, THROMBIN AND FACTOR XIII

BACKGROUND OF THE INVENTION

The invention relates to fibrin microbeads, methods for preparing the fibrin microbeads, and their use as vehicles for culturing, separating and transporting cells, as vehicles for transplanting cells involved in wound healing, and as vehicles for tissue engineering.

Fibrin clots are formed in vivo based upon the reaction of fibrinogen and thrombin in the presence of calcium ions. The initial phase of wound healing starts after the formation of fibrin clot, and involves the mobilization of cells from surrounding undamaged tissue. Normally, the earliest cells mobilized to the wound are inflammatory where they are active for a period of at least 1–3 days following injury. Subsequently, they are displaced by cells of the mesenchyme lineage which are immobilized into, navigate through and digest fibrin and replace fibrin with extracellular matrix (ECM) of different collagen types, fibronectin and hyaloron. Endothelial cells also infiltrate the fibrin and generate microcapillary structures. Ultimately, these cells replace the provisional fibrin matrix with granulation tissue populated by parenchymal cells and vasculature in secreted ECM.

Human fibroblasts are the major cellular entities responsible for the regeneration of the extracellular matrix (ECM) within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clot, help dissolve it and generate as well as reform the collagens (i.e. type I and type III) in the extracellular matrix. Based upon these properties of human fibroblasts, fibroblast implants have been suggested as a means for supplementing the body's natural wound healing regime (Gorodetsky, R., et al. *Radiat. Res.* 125:181–186 (1991)).

Benzoylated hyaluronic acid (HA) sheets containing holes or pores have been used as a carrier for fibroblasts and keratinocytes for wound healing (Andreassi, L., et al. *Wounds* 3(3): 116–126 (1991)). Specifically, HA sheets are cultured with these cells and then affixed to the site of the burn injury, where the cells migrate out of the sheet and accelerate the rate of wound re-granulation. A major problem with implanted HA sheets, however, is that they are not metabolized by tissue, are cumbersome to administer, and may result in long-term immunological problems.

Purified fibrin(ogen) (which is known in the art as a mixture of fibrin and fibrinogen) and several of its lytic fragments (i.e. FPA, FPB, D and E) have been shown to be chemotactic to a variety of cells including macrophages, human fibroblasts (HF) and endothelial cells (Gorodetsky, R., et al. *J. Lab. Clin. Med.,* in press (1997); Brown, L. F., et al. *Amer. J. Pathol.* 142:273–283 (1993); Clark, R. A. F., et al. *J. Invest. Dermatol.* 79:624–629 (1982); Ciano, P. S., et al. *Lab. Invest.* 54:62–69 (1986); Dejana, E., et al. *J. Clin. Invest.* 75:11–18 (1985)). Thrombin also has been shown to exert proliferative effect on various cells including fibroblasts, endothelial cells, and to enhance wound healing in rat skin (Kang, Y. H., et al. *J. Histochem. Cytochem.* 39:413–423 (1991); Shuman, F., *NY Acad. Sci.* 408:228–235 (1986); Biedermann, B., et al. *J. Lab. Clin. Med.* 124:339–347 (1994)).

Fibrin microbeads have been described in the prior art for use as drug delivery systems ((Ho, et al. *Drug Dev. and Ind. Pharm.* 20(4):535–546 (1994); Senderoff, et al. *J. Parenteral Sci. & Tech.* 45(1):2–6 (1991)). However, it has not been suggested or taught in the prior art that such fibrin microbeads have chemotactic and/or proliferative effects on any cells. Furthermore, the fibrin microbeads of Ho, et al. and Senderoff, et al. would not be particularly useful or desirable as vehicles for culturing cells. In this regard, the Ho, et al. microbeads contain glutaraldehyde which cross-links proteins and destroys certain biologically active sites, thereby interfering with the binding of the microbeads to cells. Glutaraldehyde treatment may also render the microbeads immunogenic. The Senderoff, et al. microbeads contain essentially the same relatively low degree of cross-linking as fibrin. Thus, the Senderoff, et al. microbeads are not stable in aqueous solutions and therefore would not be useful as vehicles for culturing cells which require matrices that do not readily dissolve in aqueous solutions.

SUMMARY OF THE INVENTION

The present invention provides fibrin microbeads that, unlike the fibrin microbeads of the prior art, do not contain any exogenous cross-linking agents such as glutaraldehyde that can damage certain biologically active sites that permit the microbeads to react with various types of cells. In addition, the fibrin microbeads of the present invention, unlike the prior art fibrin microbeads, contain extensive cross-linking of fibrin(ogen) which renders the fibrin microbeads stable for prolonged periods in aqueous solution, a property which is particularly desirable for use as vehicles for culturing cells, and for other uses.

Accordingly, it is an object of the present invention to provide fibrin microbeads that are biologically active and comprise extensively cross-linked fibrin(ogen).

It also is an object of the present invention to provide a method for preparing the fibrin microbeads of the present invention.

It is a further object of the present invention to provide a composition comprising cells bound to the fibrin microbeads of the present invention.

It is a still further object of the present invention to provide methods for culturing and separating one cell type from another using the fibrin microbeads of the present invention.

In addition, it is an object of the present invention to provide a method for transplanting cells using the fibrin microbeads of the present invention.

It also is an object of the present invention to provide a method for promoting healing of a wound using cells bound to the fibrin microbeads of the present invention.

Finally, it is an object of the present invention to provide a method for engineering tissue using the fibrin microbeads of the present invention.

Additional objects of the present invention will be apparent from the description which follows.

BRIEF DESCRIPTION OF THE FIGURES

FIG. 5A shows the FMB and fibroblasts in culture, while FIG. 6A shows fibroblasts leaving FMB after being transferred to a new culture flask.

DETAILED DESCRIPTION OF THE INVENTION

Figure 1:
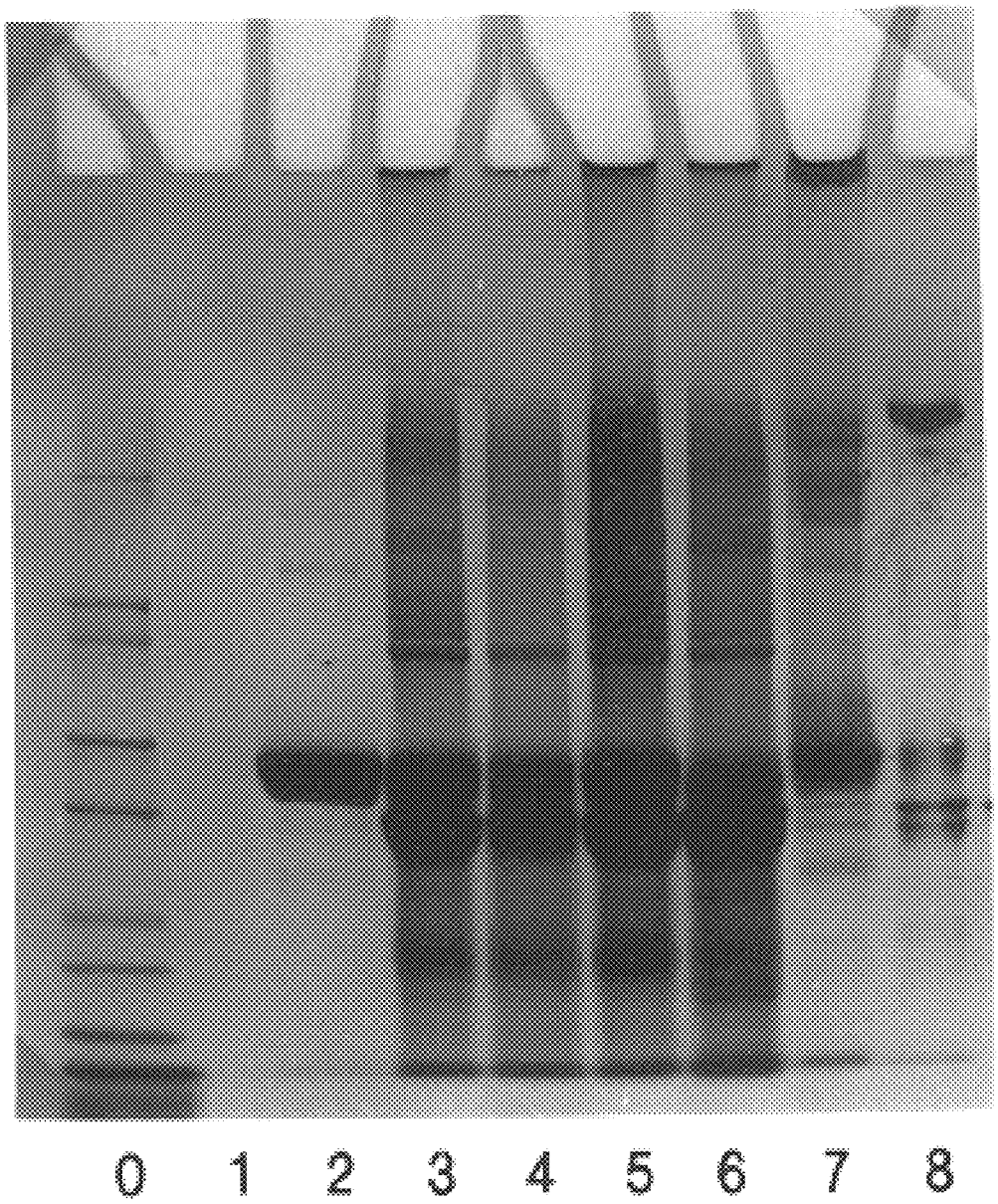
FIG. 1 represents an SDS-PAGE (non-reduced) of various FMB preparations of the present invention (lanes 3–7) in comparison with albumin (lane 2) and fibrin (lane 8). Lane 0 represents molecular weight (MW) marker, while lane 1 is blank. The results show that the fibrin microbead ("FMB") preparations of the present invention (lanes 3–7) are more extensively cross-linked than fibrin (lane 8).

The present invention is directed to biologically active, fibrin microbeads comprising extensively cross-linked fibrin (ogen). As used herein, "biologically active" means that the fibrin microbeads possess biologically active sites that permit the microbeads to attract and facilitate the growth of various types of cells. This is different than fibrin microbeads of the prior art that are treated with exogenous cross-linking agents, such as glutaraldehyde, which render fibrin microbeads unattractive to cells and biologically inactive.

"Extensively cross-linked" means that the fibrin(ogen) contains at least 30% cross-linked fibrin(ogen), and more preferably at least 50% cross-linked fibrin(ogen). The extensive cross-linking of the fibrin microbeads of the present invention is believed to occur during their manufacture, which utilizes high temperatures that help denature the native fibrin(ogen) structure, specifically the D-domain, thereby exposing sites for cross-linking by factor XIII, which are not normally cross-linked by native conformers of fibrin(ogen) at ambient temperatures. The SDS-PAGE gel patterns (FIG. 1) show extensive cross-linking due to such factor XIII mediated reactions. The extensive cross-linking renders the microbeads of the present invention insoluble and stable in an aqueous environment, thus rendering the microbeads stable for cell culturing and other uses.

It also is within the confines of the present invention that the fibrin microbead also may comprise at least one bioactive agent. Suitable bioactive agents include but are not limited to drugs, neurologics, vitamins, vitamin derivatives, growth factors, glucocorticosteroids, steroids, antibiotics, antibacterial compounds including bacteriocidal and bacteriostatic compounds, antiviral compounds, antifungal compounds, antiparasitic compounds, tumoricidal compounds, tumoristatic compounds, toxins, enzymes, enzyme inhibitors proteins, peptides, minerals, neurotransimitters, lipoproteins, glycoproteins, immunomodulators, immunoglobulins and fragments thereof, dyes, radiolabels, radiopaque compounds, fluorescent compounds, fatty acid derivatives, polysaccharides, cell receptor binding molecules, antiinflammatories, antiglaucomic compounds, mydriatic compounds, anesthetics, nucleic acids, polynucleotides, and the like.

The fibrin microbeads of the present invention are produced in the following manner. First, an aqueous solution comprising fibrinogen, thrombin and factor XIII is prepared. This solution may be prepared by combining fibrinogen containing endogenous factor XIII with thrombin, by combining cryoprecipitate containing endogenous fibrinogen and endogenous factor XIII with thrombin, or by combining fibrinogen, factor XIII and thrombin individually into an aqueous solution. It also is within the confines of the present invention that equivalent proteases such as snake venom proteases (e.g. reptilase) may be used as an alternative to thrombin. The ratio of fibrinogen:thrombin:factor XIII in the aqueous solution is preferably 5–100 mg/mL:1–100 U/mL:1–50 U/mL, and most preferably 20–40 mg/mL:5–10 U/mL:2–20 U/mL. In addition to these proteins, the aqueous solution also may contain fibronectin and other bloodderived proteins that may be present in the fibrinogen and cryoprecipitate starting materials. If it is desired for the fibrin microbead to contain any bioactive agents, then those agents can be added into the fibrinogen or thrombin solutions prior to their mixing, or directly to the aqueous solution.

Next, prior to the onset of coagulation, the aqueous solution is introduced into an oil heated to a temperature in the range of about 50–80° C. to form an emulsion. A hydrophobic organic solvent such as isooctane also may be included in the oil. The inventors have found that using the concentrations of fibrinogen and thrombin presented in the Experimental Details Section below, coagulation occurs at about 30 seconds after the fibrinogen and thrombin are combined. However, for other concentrations of fibrinogen and thrombin, the onset of coagulation can be determined by using known coagulation assays.

Suitable oils include but are not limited to vegetable oils (such as corn oil, olive oil, soy oil, and coconut oil), petroleum based oils, silicone oils, and combinations thereof. Vegetable oils are preferred because they can be metabolized by cells and may provide nutrients to the cells. In the most preferred embodiment, the oil is corn oil. The inventors believe that minerals oils should be avoided since they are not metabolized by cells. In addition, oils that contain unsaturated bonds (i.e. Canola oil) should be avoided since they may be oxidized.

After the aqueous solution is introduced into the heated oil, the emulsion is then maintained at a temperature of about 50–80° C. and mixed at an appropriate speed until fibrin microbeads comprising extensively cross-linked fibrin (ogen) are obtained in the emulsion. The mixing speed will depend upon the volume of the emulsion, and the desired size of the microbeads. For volumes of 400 mL oil and 100 mL aqueous phase in a 1 L flask, the preferred mixing speed is 300–500 rpm. The emulsion is generally mixed for about 3–9 hours, although the actual time will vary depending upon the temperature, the concentration of the initial reactants and the volume of the emulsion. As discussed above, it is believed that at temperatures of about 50–80° C., the native fibrin(ogen) structure denatures exposing sites for cross-linking by factor XIII, which are not normally crosslinked at ambient temperatures. Such cross-linking occurs during the first phase of the mixing/heating cycle. The heating also serves the purpose of dehydrating the emulsified system (drying process) thereby producing cross-linked fibrin(ogen) particles that do not stick together or coalesce, as such particles do when they possess too much water.

Finally, the extensively cross-linked fibrin microbeads may be isolated from the emulsion using procedures such as centrifugation, filtration, or a combination thereof. The isolated fibrin microbeads may then preferably be washed with solvents such as hexane, acetone and/or ethanol, and then air dried. The microbeads may then be graded to the desired size using commercially available filters or sieves. Preferably, the fibrin microbeads of the present invention are graded to a diameter of about 50–200 microns, although larger or smaller fibrin microbeads may be sized, if desired.

The present invention also provides a composition comprising cells bound to the fibrin microbeads of the present invention. The cells include any cells that bind to the fibrin microbeads. Such cells include but are not limited to fibroblasts, endothelial cells, chondrocytes, neuroblastoma cells, kidney cells, liver cells, pancreatic cells, thyroid cells, glial cells, smooth muscle cells, mouse mammary carcinoma cells, bone/cartilage forming cells, and combinations thereof.

As certain cells also proliferate on the fibrin microbeads, the present invention also provides a method for culturing fibrin microbead binding cells with the fibrin microbeads of the present invention in a culture medium under conditions permitting the cells to bind to the fibrin microbeads. The advantage of culturing cells with the fibrin microbeads of the present invention is that the cells bind and grow on the fibrin microbeads. Thus, as the cells are needed for other uses, they may be easily removed from the cell culture medium by pipeting or pouring off the fibrin microbeads without trauma to the cells. This is a substantial improvement over conventional means for removing cells from culture plates such as trypsinization, which may damage certain receptors on the cells and otherwise cause trauma to the cells. The ability to transfer cells from one environment to another using the fibrin microbeads of the present invention also means that such cells can be reseeded into fresh culture medium with minimal damage to the cells.

In addition to these advantages, the fibrin microbeads of the present invention, because they attract and grow a population of cells that is significantly more dense than conventional cell cultures, can be used as a more efficient means for producing recombinant proteins, viruses, bacteria, the cloning of desirable nucleic acids, and the like, than conventional cell cultures. As such, it is envisioned that the cells cultured in connection with the fibrin microbeads of the present invention can be transformed or transfected with various vectors, viruses, bacteria, nucleic acid, and the like. In this manner, the fibrin microbeads of the present invention can be used as vehicles for the production of viruses, recombinant proteins, cloning of nucleic acids, and the like.

In addition, because not all cells bind to the fibrin microbeads of the present invention, the fibrin microbeads also are very useful for separating cells. In this regard, the present invention also provides a method for separating cells that bind to fibrin microbeads from a cell culture containing the fibrin microbead binding cells and cells that do not bind to fibrin microbeads. In this method, cells can be cultured with the fibrin microbeads in a growth medium under conditions permitting the fibrin microbead binding cells to bind to the fibrin microbeads. The cells of interest that bind to the microbeads can then be isolated from the culture medium by removing the fibrin microbeads.

Furthermore, because the fibrin microbeads of the present invention bind certain cells it also is envisioned that the microbeads can be used as a vehicle for transplanting such cells. For example, because the fibrin microbeads of the present invention bind cells involved in wound healing, the fibrin microbeads can be used to transplant wound healing promoting cells into a wound. As used herein, "wound" includes surgical wounds, burns, ulcers, lacerations, and the like. This can be accomplished by culturing the desired cells with the fibrin microbeads, and applying a wound healing effective amount of the cells bound to the fibrin microbeads to the wound. Suitable wound healing promoting cells include but are not limited to fibroblasts, smooth muscle cells, endothelial cells, chondrocytes, bone/cartilage forming cells and combinations thereof. It also is within the confines of the present invention that the fibrin microbeads may further comprise at least one bioactive agent selected from the group consisting of wound healing promoting agents, growth factors, glucocorticosteroids, steroids, antibiotics, antibacterial compounds, antiviral compounds, and antifungal compounds. The composition may be affixed to the wound using fibrin glue.

In addition, it also is envisioned that the fibrin microbeads may be used for transplanting cells that have been modified by known recombinant methods to express desirable proteins for treating diseases associated with a deficiency of these proteins. For example, vectors containing nucleic acid encoding insulin may be used to incorporate the nucleic acid into the cells by known recombinant techniques so that the cells express insulin. The insulin producing cells can then be cultured with the fibrin microbeads of the present invention and then introduced into the patient for treating diabetes. Other diseases that may be treated include but are not limited to hemophilia A (factor VIII deficiency), hemophilia B (factor IX deficiency) and cystic fibrosis.

Finally, because the fibrin microbeads of the present invention also bind cells involved in the formation of tissue, it is envisioned that the fibrin microbeads can also be used as a vehicle for facilitating tissue engineering. In this connection, a suspension of the desired cells can be prepared by culturing the cells with the fibrin microbeads. The suspension of the fibrin microbeads carrying the desired cells can then be applied to a surface of a prosthetic device using fibrin glue, for example, and the cells cultured in a tissue culture medium until the desired extracellular matrix or tissue is formed on the surface of the prosthetic device. The choice of cells will depend upon the tissue desired and include but are not limited to fibroblasts, endothelial cells, chondrocytes, neuroblastoma cells, kidney cells, liver cells, pancreatic cells, thyroid cells, glial cells, smooth muscle cells, bone/cartilage forming cells, and any combination thereof.

The present invention is described in the following Experimental Details Section which is set forth to aid in an understanding of the invention, and should not be construed to limit in any way the invention as defined in the claims which follow thereafter.

EXPERIMENTAL DETAILS SECTION

Materials and Methods

Proteins

The source of fibrinogen used in the experiments was either fibrinogen prepared by fractionation of pooled plasma, or cryoprecipitate obtained from frozen and thawed pooled plasma. The biochemical composition of the purified fibrinogen was as follows: $41\pm5$ mg/mL protein, $40\pm5$ mg/mL fibrinogen, $1\pm1$ mg/mL fibronectin, trace IgG and $20\pm10$ U/mL Factor XIII. The biochemical composition of the pooled cryoprecipitate was as follows: 72±10 mg/mL protein, 13±5 mg/mL fibrinogen, 3±1 mg/mL fibronectin, 13±2 mg/mL IgG and 5±1 U/mL Factor XIII. Thrombin was either bovine or human, with unitage determined by clot time assays calibrated against an international standard.

FMB Preparation Protocol

A typical preparation was carried out by heating 400 mL corn oil and isooctane to 55° C. with mechanical stirring. A solution of 25 mL fibrinogen (40 mg/mL) or cryoprecipitate (diluted 1:2 in Tris/saline buffer) was mixed with 5 mL thrombin to 5 U/mL (final concentration). This level induced coagulation within 30 seconds. After adding the thrombin but before coagulation occurred, the protein mixture was slowly added to the heated oil so that the stirring dispersed the aqueous phase into droplets suspended in the oil. Mixing and heating was continued for 1 hour. The isooctane evaporated out of the oil eventually, after which the temperature was elevated to approximately 75° C. Mixing continued for 4–8 hours. The heat was then turned off and stirring continued for 2 hours until the mixture reached room temperature.

The oil suspension was rendered less viscous by adding 100 mL hexane, filtered through a Whatman #42 filter paper, and the particulate FMB was rinsed with hexane. The crude FMB was then suspended in 50 mL 95% ethanol and homogenized for 1 minute. The FMB particles were allowed to settle for 10–20 seconds and the supernatant "fines" decanted. These procedures were repeated three times, after which the fibrin microbeads of the present invention ("FMB") were air dried, weighed and stored at 4° C. For sizing, the FMB were passed through a wire mesh to select for FMB of around 50–200 micron diameter.

Prior Art Fibrin Microbeads

Fibrin microbeads were prepared essentially as described in Senderoff, et al., "Fibrin Based Drug Delivery Systems," *J. Parenteral Sci. & Tech.*, 45(1):2–6 (1991). Specifically, a fibrinogen solution was prepared from 50 mg of desalted, freeze-dried fibrinogen and 1.0 mL citrate buffer. The solution was then mixed with 2.5 units of thrombin, injected into 50 mL of heavy mineral oil, and then stirred at 1500 rpm. After a 30 minute incubation, the microparticles were separated and washed with ethyl acetate and 0.05% Tween 80. The microparticles were then dried over nitrogen gas to remove organic solvents.

Solubility Tests

The FMB of the present invention were tested for solubility in Tris/saline or in 4 M urea monitored by phase contrast microscopy. Neither the Tris buffer nor the 4 M urea dissolved the FMB for up to 1 week at room temperature, though the latter did induce some swelling.

SDS-PAGE

Figure 2:
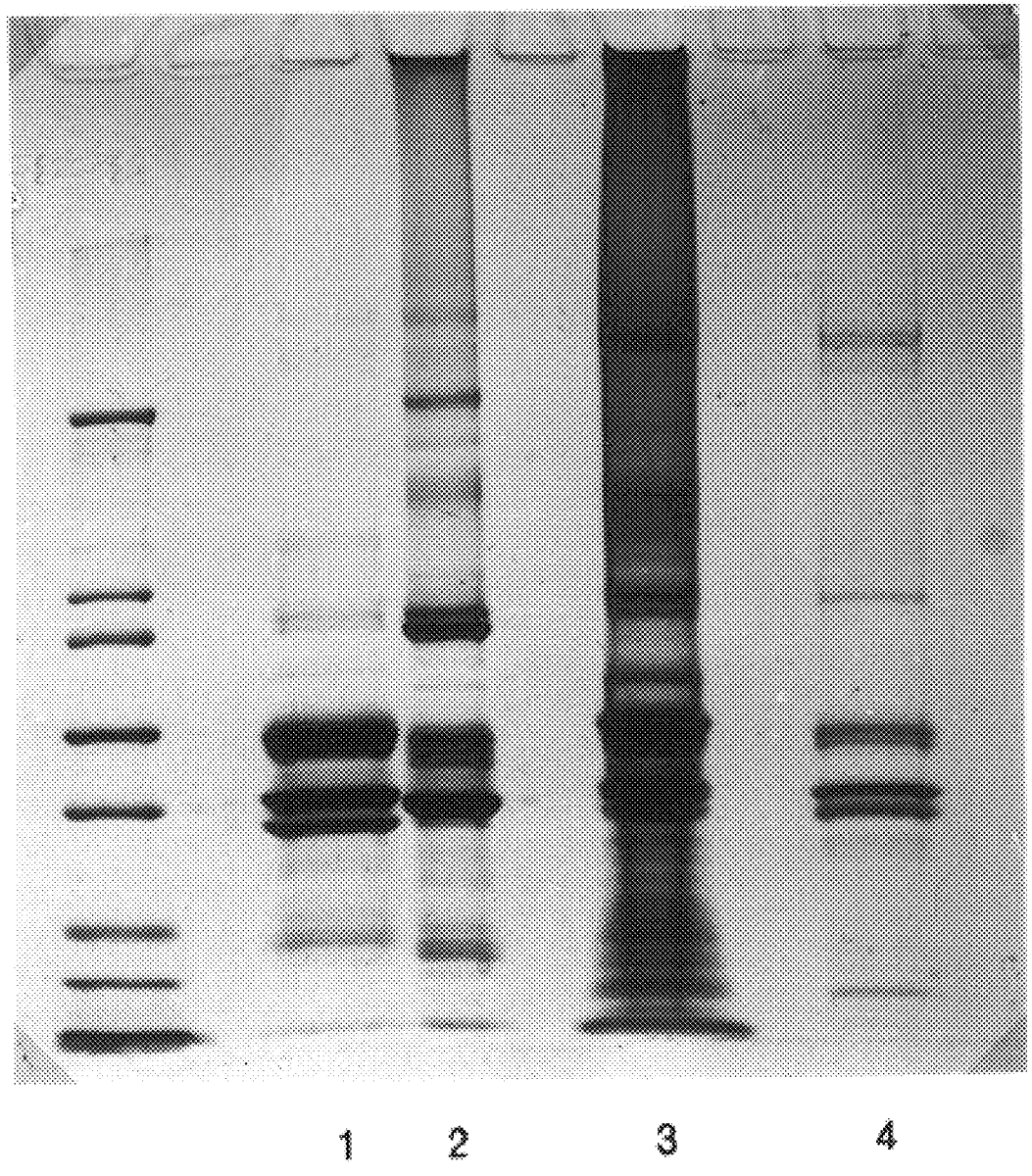
FIG. 2 represents an SDS-PAGE (reduced) of FMB preparation of the present invention (lane 3) in comparison with fibrinogen (lane 1), fibrin (lane 2) and microbead of Senderoff, et al. (1994) (lane 4). Lane 0 represents molecular weight (MW) marker. The SDS-PAGE shows that the FMB preparation (lane 3) of the present invention is significantly more cross-linked than fibrinogen (lane 1), fibrin (lane 2) and the microbead of Senderoff, et al. (1994) (lane 4).

Reduced SDS-PAGE of various FMB preparations of the present invention were carried out and compared to SDS-PAGE of albumin and fibrinogen. As shown in FIG. 1, the SDS-PAGE of FMB preparations of the present invention showed multiple cross-links far beyond that observed with fibrinogen. Similarly, SDS-PAGE was carried out for the FMB of the present invention and compared to SDS-PAGE of fibrinogen, fibrin and the microbead of Senderoff, et al. (1994). The results are presented in FIG. 2 and show that the FMB preparation of the present invention (lane 3) is significantly more cross-linked than fibrinogen (lane 1), normal clottable fibrin (lane 2) (which usually shows only γ—γ dimers, loss of α and γ bands and α—α multimers which do not enter the SDS-PAGE gel) and the microbead of Senderoff, et al. (1994) (lane 4).

Densitometric Tracings

Figure 3A:
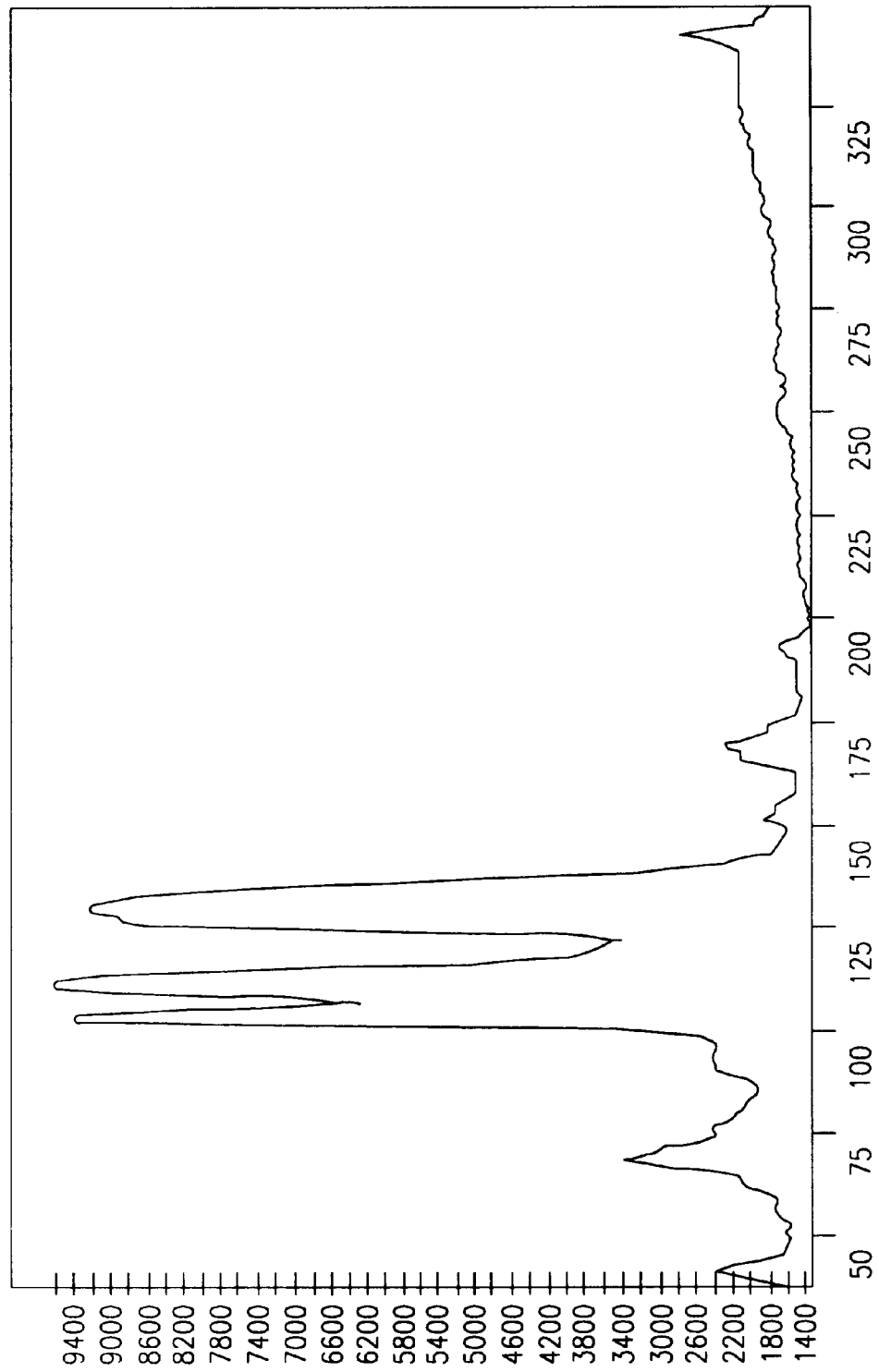
FIGS. 3A–3D represent densitometric tracings of fibrinogen (FIG. 3A), fibrin (FIG. 3B), the microbead of Senderoff, et al. (1994) (FIG. 3C) and the FMB preparation of the present invention (FIG. 3D). The densitometric tracings show that the FMB preparation of the present invention (FIG. 3D) is significantly more cross-linked than fibrinogen (FIG. 3A), fibrin (FIG. 3B) and the microbead of Senderoff, et al. (1994) (FIG. 3C).
Figure 3B:
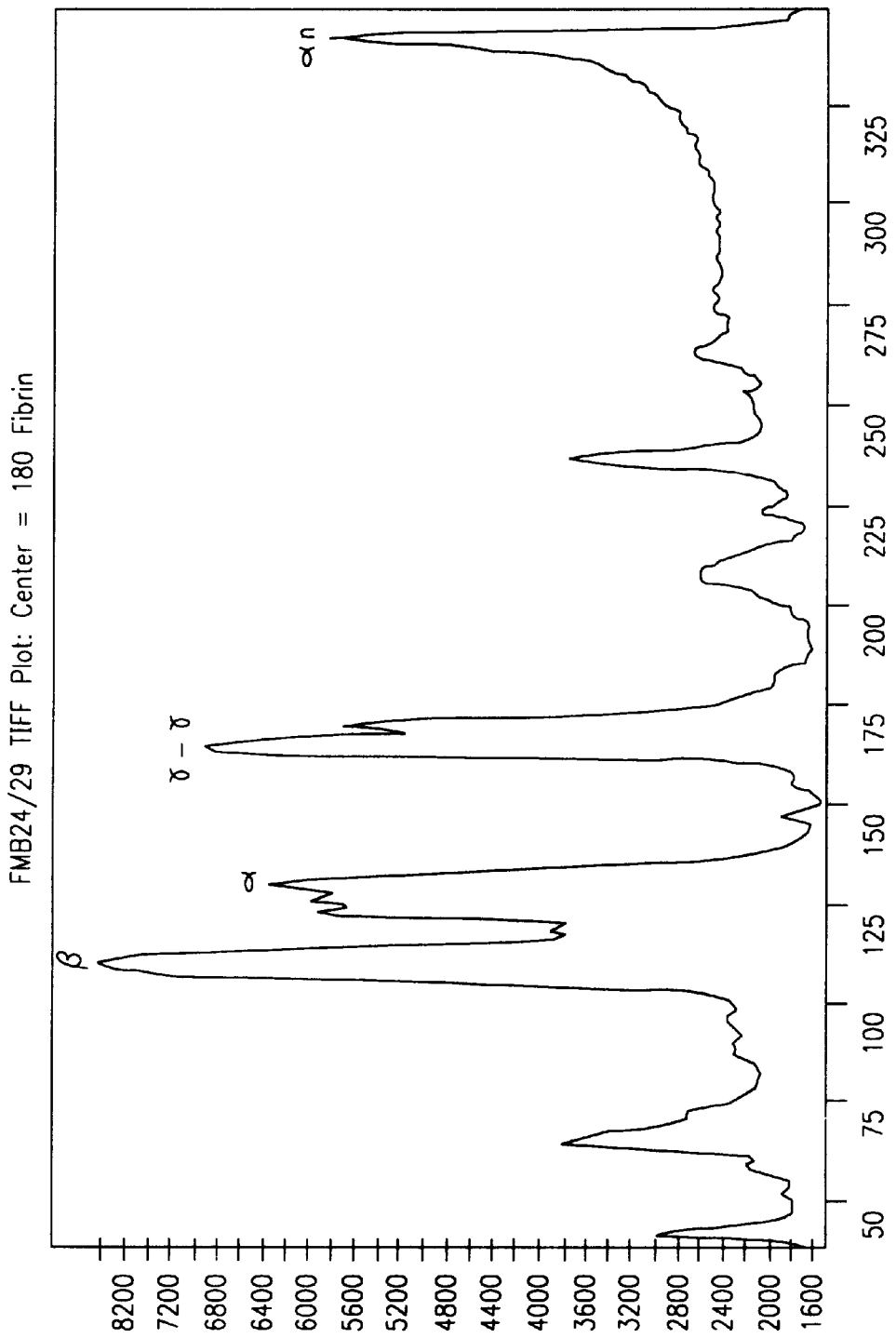
Figure 3C:
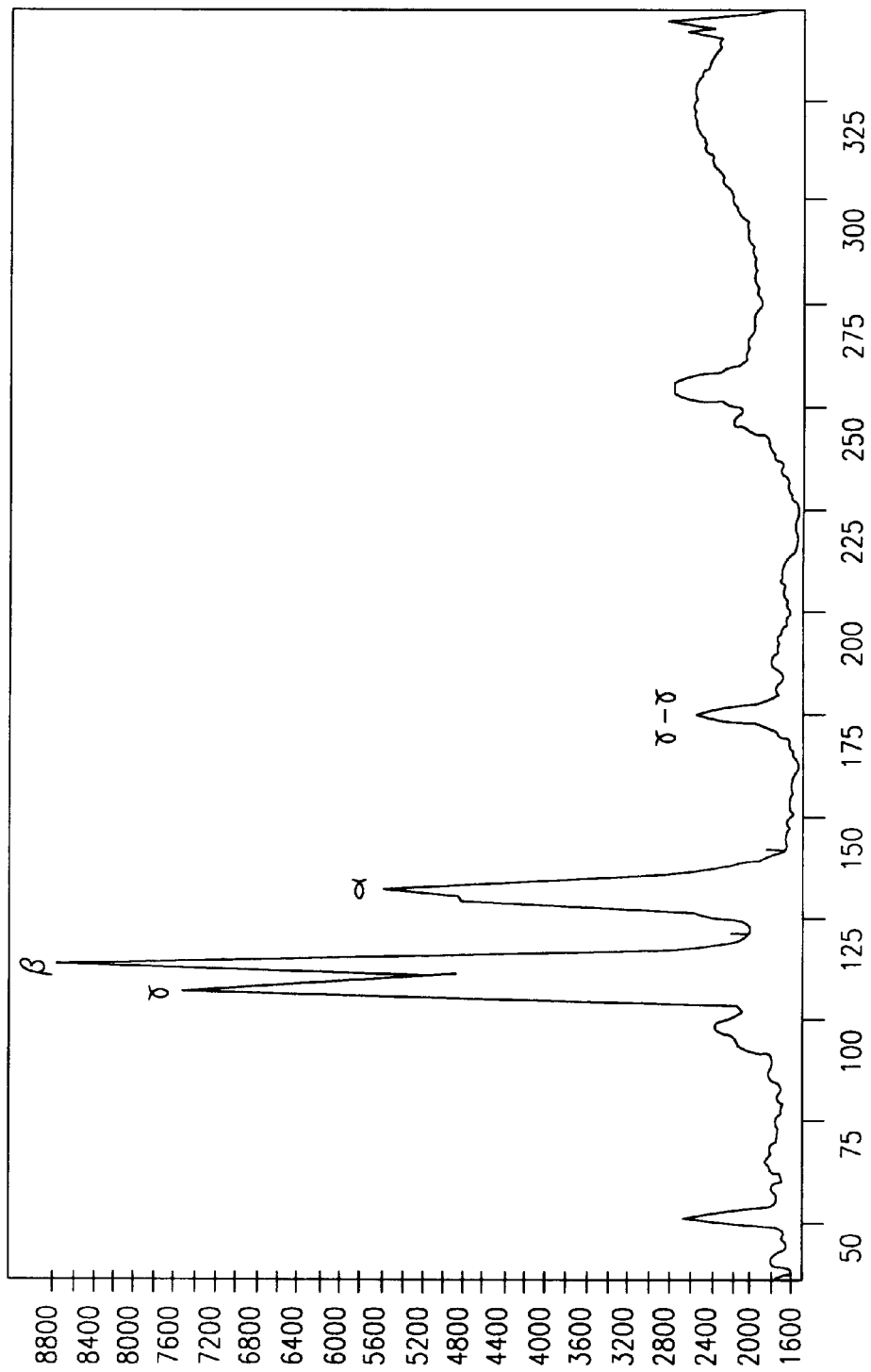
Figure 3D:
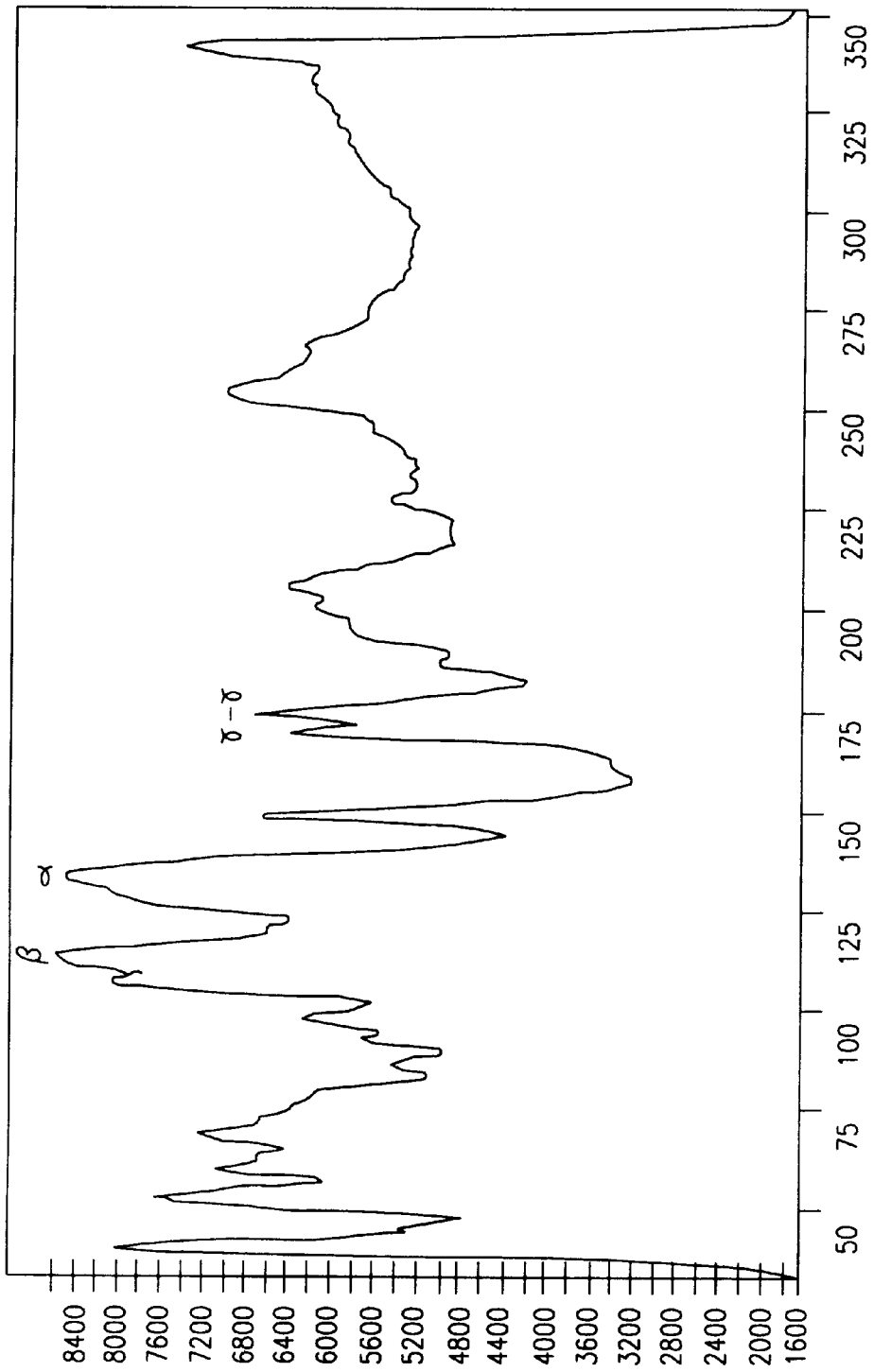

Densitometric tracings were prepared for fibrinogen, fibrin, the microbead of Senderoff, et al. (1994) and an FMB preparation of the present invention. Briefly, the SDS-PAGE (reduced) gel was scanned on a flat-bed scanner linked to a Mac-TCI-II computer. The optical density of the bands were digitalized and the resultant tracings are presented in FIGS. 3A–3D. As shown in the figures, the FMB preparation of the present invention (FIG. 3D) is significantly more cross-linked than fibrinogen (FIG. 3A), fibrin (FIG. 3B) and the microbead of Senderoff, et al. (1994) (FIG. 3C).

Cell Cultures

Normal human fibroblasts (HF) were isolated from the foreskin of young human subjects who underwent voluntary circumcision. The dermal layer of skin was chopped and digested briefly by 0.25% trypsin/versen. The isolated cells were washed and plated on plastic Petri dishes with DMEM supplemented by 10% fetal calf serum (FCS), antibiotics, and glutamine. The plates were washed after 10 hrs to select for the better attached fibroblasts. After 3–4 passages, the cells microscopically consisted of a homogenous population of fibroblasts. Immunohistology with monoclonal anti-human-fibroblast surface proteins (Product F4771, Sigma, Rehovot, Israel) of cells isolated and grown in these conditions confirm that this procedure yields homogeneous fibroblast culture (Ronnov-Jessen, L., et al. *Histochem. Cytochem.* 40:475–486 (1992)).

Normal murine fibroblasts (MF) were isolated from the skin of 2–3 days old neonate C3H mice by 3 step digestion, each for 2 hrs, with trypsin/versen. The use of neonate mice with low cross linking of collagen enables the isolation of high yield of cells during the proteolytic digestion. The details of the rest of the protocol are similar to those used for the isolation and growth of HF. The cells were cultured similarly to the HF and the homogeneity of these cells following 3–5 passages was obvious microscopically. These cells could be grown for at least 12–14 passages before any slow-down in their rate of proliferation occurred. The cells from the 4th to the 10th passage were used.

Porcine smooth muscle cells (SMC) were isolated from thoracic aortas of young animals and kept in culture with twice medium change and splitting once in 1–2 weeks. Cells of up to 10 passages were used. The purity of the SMC culture was measured by immunohistology with monoclonal anti-muscle-specific-actin HHF-35 (Bar-Shavit, R., et al. *Cell Regul.* 1:453–463 (1990)).

Other cell lines were obtained from different sources and cultured in their standard conditions as described in the following references: murine fibroblast line (3T3) and normal human keratinocytes from Dr. H. Ben-Bassat (Ben-Bassat, H., et al. *Plastic & Reconstructive Surgery* 89:510–520 (1992)); murine mast cells (MC-9) from Dr. E. Razin (Razin, E. and G. Marx *J. Immunol.* 133:3282–3285 (1984)); normal bovine aortic endothelial cells (BAEC) from Dr. I. Vlodavsky (Vlodavsky, I., et al. *J. Cell Biol.* 83:468–486 (1979)); porcine smooth muscle from Dr. H. Shwalb, were isolated and cultured as previously described (Bar-Shavit, R., et al. *Cell Regul.* 1:453–463 (1990)); murine leukemic cells (P-388) from Dr. A. Ramu (Ramu, A., et al. *Biochem. Pharmacol.* 42:1699–1704 (1992)); human ovarian carcinoma cells (OV-1063) were isolated by Dr. A. Horowitz (Horowitz, A. T., et al. *Oncology* 42:332 337 (1985)); murine mammary adenocarcinoma cells (EMT-6) were grown at their standard conditions (Rockwell, S. *Br. J. Cancer* 37:212–215 (1978)); and murine macrophage-like cells (J774.2) were obtained from Dr. I. Ringel (Ringel, et al. *Cancer Res.* 45:3856–3863 (1985)).

All culture medium ingredients were purchased from Biological Industries (Beit-HaEmek, Israel) and fetal calf serum was supplied by GIBCO (Grand Island, New York, N.Y., U.S.A.). The cell cultures were maintained at 37° C. in water-jacketed $CO_2$ incubators, and were harvested by trypsin/versen solution with 1–2 passages per week in a split ratio of 1:10 for fast proliferating transformed cells and 1:4 for normal cell types.

FMB Cell Culture Studies

For FMB cell culture studies, $10^6$ cells were grown in 10% serum DMEM medium in a 50 mL culture flask to near confluence. The cells were trypsinized, harvested and counted. A 50 mL polycarbonate tube (punctured top) covered loosely with aluminum foil was then prepared. 0.5 mL of FMB (sterilized with 70% alcohol over night, rinse 3× or gamma-irradiate, 5 Gy) were then added into the tube with 5 mL of the culture medium. 10 million of the trypsinized cells per 0.3 mL of medium packed beads were then transferred into the polycarbonate tube filled with 5–6 mL medium. The tubes were then placed in tissue culture incubator on a test tube rotator that was placed titled in about 20 degrees so that the tubes rotate sidewise in about 30 rpm and the medium does not reach the punctured test tube top cover. The tubes were vortexed once every 2 days for 10 seconds to prevent beads from clumping to each other through the cells. Medium was exchanged once every 2–3 days. After the initial 2–3 days of incubation, the tube was shaken gently and the suspension aliquot was removed. The unbound cells were counted using the MTS assay (the CellTitre 96 AQueous Assay by Promega). The results with FMB in comparison with fibrinogen-coated Sepharose Beads (SB-Fib) are presented in the table below:

| Cell Binding to FMB or SB-Fib (% at 4 days) | | |
|---|---|---|
| | % Cells Bound | |
| | FMB | SB-Fib |
| Normal Cells | | |
| Human fibroblasts | 94 | 71 |
| Mouse fibroblasts | 93 | 81 |
| Human keratinocyte | 0 | 0 |
| Pig aortic smooth muscle | 98 | 74 |
| Mouse mast cell | 0 | 0 |
| Transformed Cells | | |
| 3T3 mouse fibroblast | 98 | 90 |
| OV-1063 human ovarian carcinoma | 0 | 0 |
| EMT-6 mouse mammary carcinoma | 94 | 62 |
| J774.2 mouse macrophages | 0 | 0 |
| P388-S mouse leukemia | 0 | 0 |

SEM/CFM Analysis

Figure 4:
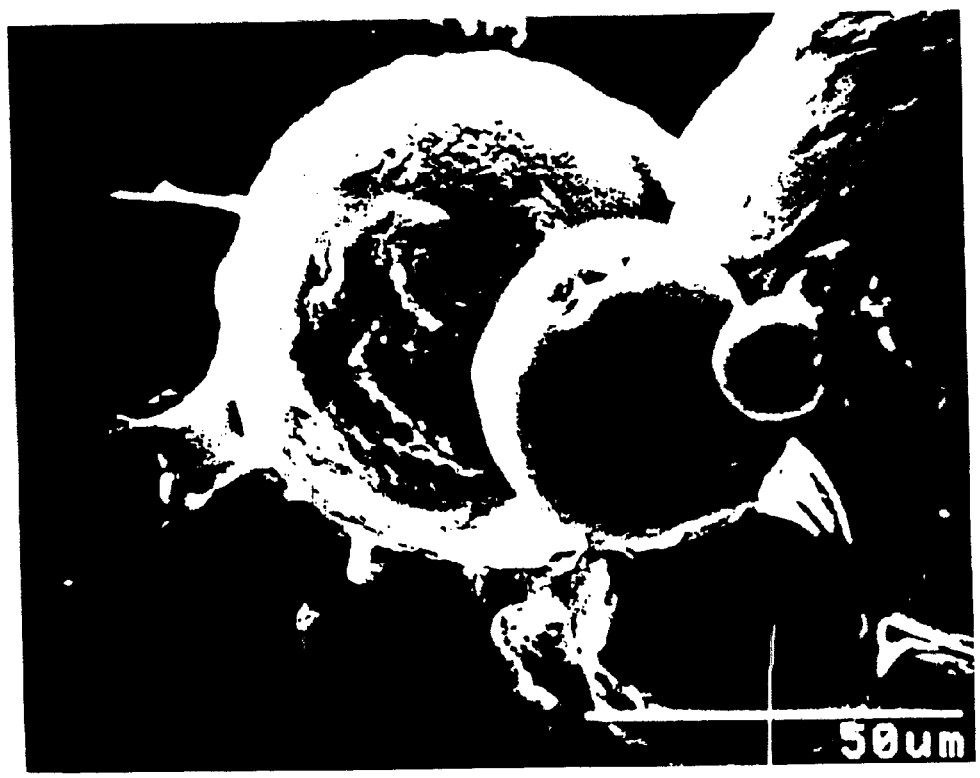
FIG. 4 represents a scanning electron micrograph of FMB of the present invention with fibroblasts, and shows how closely the cells are bound to the surface of the FMB.
Figure 5A:
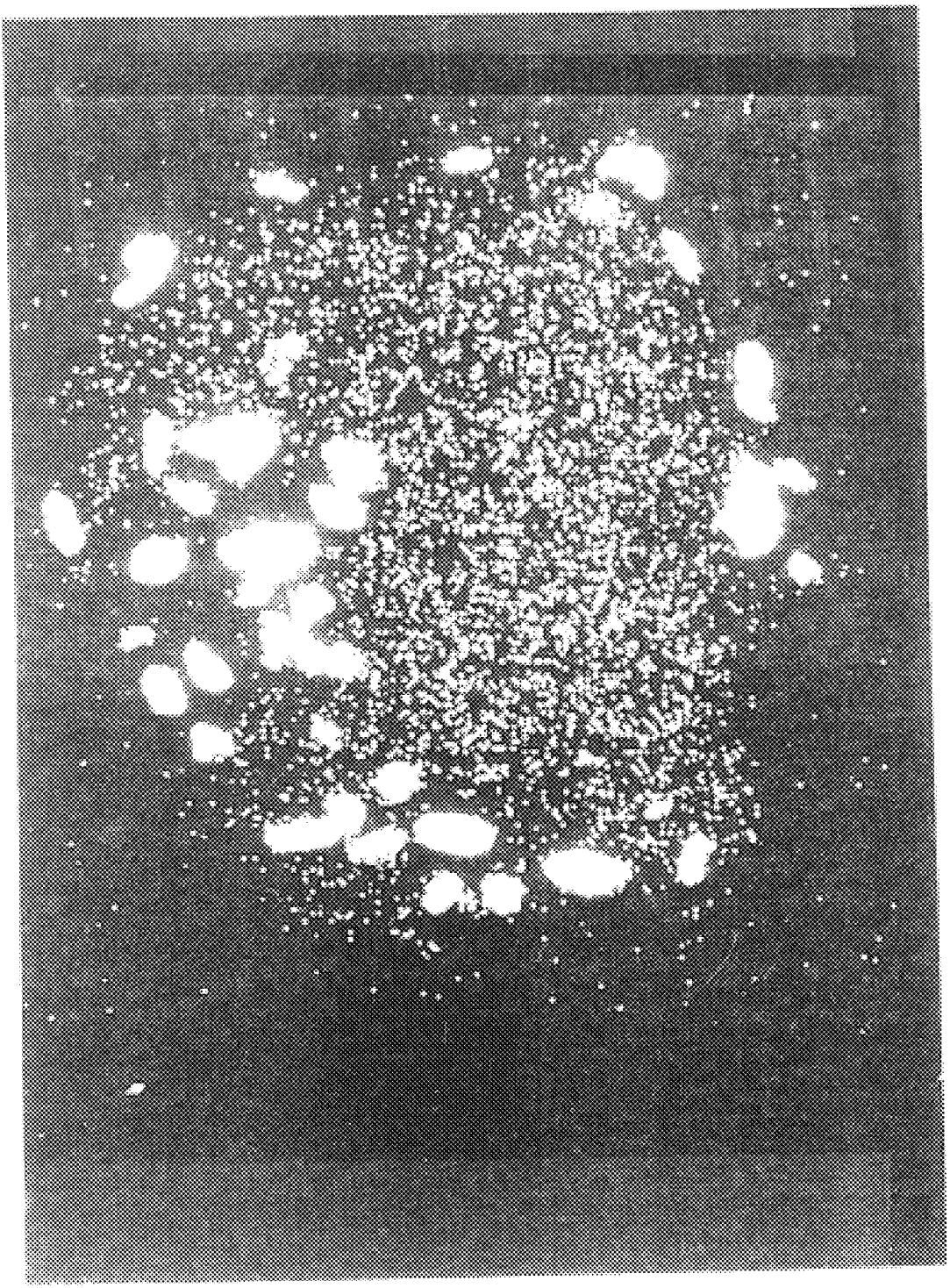
FIGS. 5A and 5B represents fluorescent micrograph of FMB of the present invention with human fibroblasts visualized by a computerized fluorescence microscope.
Figure 5B:
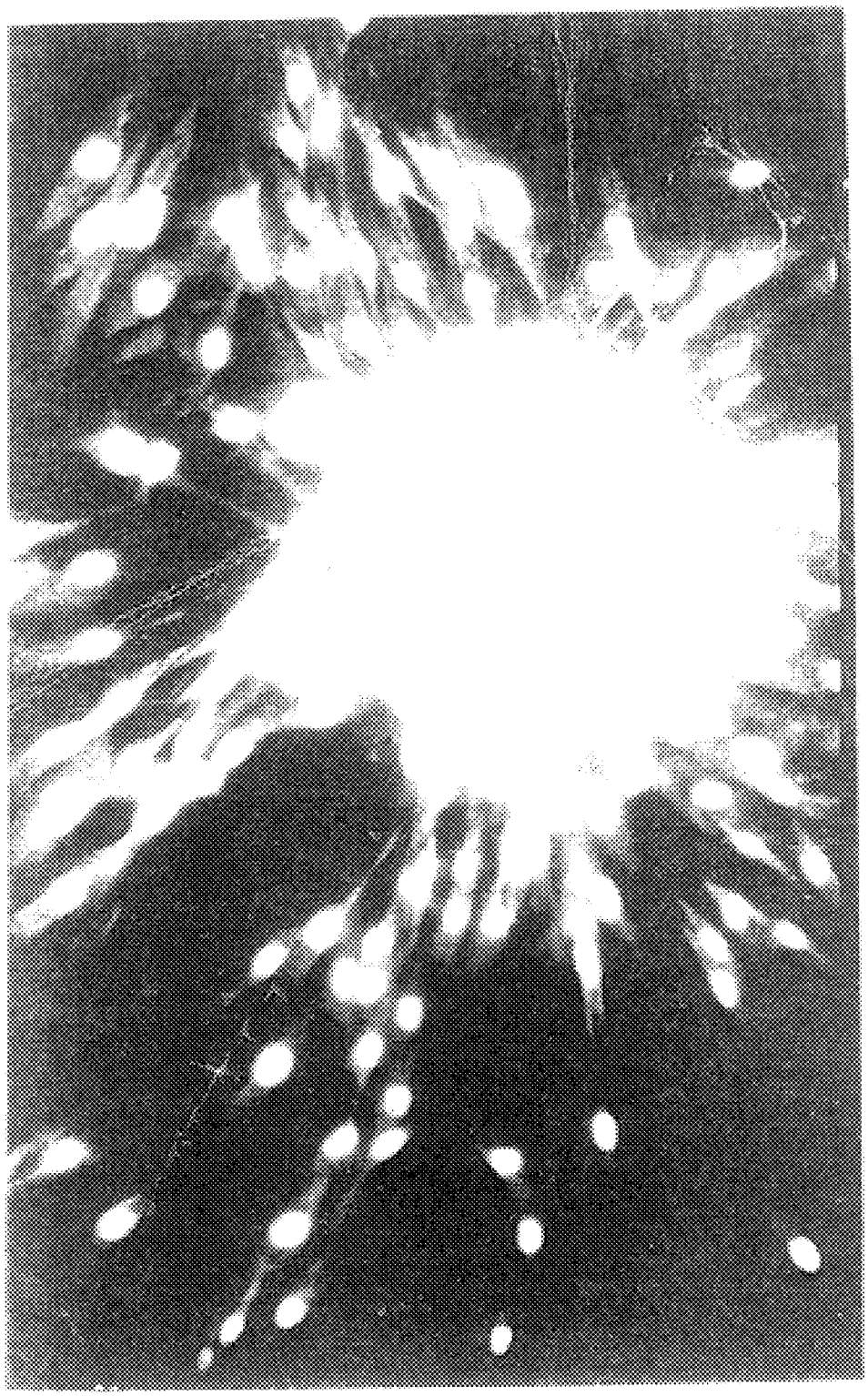

FMB with cells were prepared for scanning electron microscopy (SEM) by removing 200 µL FMB with cells from the culture medium and fixing by making up to 2% glutaradehyde. Samples were further processed by critical point drying, coated with osmium tetroxide, sputter coated with Au/Pd and examined with a Hitachi S-530 Scanning Microscope. A scanning electron micrograph of FMB of the present invention with fibroblasts shows that the cells are bound to the surface of the FMB (see FIG. 4). A fluorescent micrograph of FMB of the present invention with human fibroblasts also was performed with a computerized confocal fluorescence microscope, and the photograph of this micrograph is shown in FIGS. 5A and 5B.

Cell Viability/Cell Density Studies

In order to determine how long cells could remain viable on FMB, human fibroblasts on FMB were maintained in culture medium and the viability was determined by measuring viable cell density in constant volume samples of evenly distributed FMB loaded with cells using the MTS proliferation assay (the CellTitre 96 Aqueous Assay by Promega). It was found that FMB can be used to maintain a high cell density of viable cells for up to three weeks with initial proliferation until high density confluence of cells on beads was reached. Cell density was increased from $9.6 \times 10^5$ cells/mL to $3.6 \times 10^6$ cells per mL with 166 mg FMB.

In another experiment, EMT-6 mouse mammary carcinoma cells were loaded on FMB as follows. The cells were harvested and 3–5 million cells were added to rotating 50 mL polycarbonate tubes each with about 0.5–0.6 mL packed beads in 5–6 mL cell culture medium and rotated. Medium was exchanged on the beads every 2–3 days. After 6 days, almost total confluence of cells was recorded on the beads with cell density of about $50 \times 10^6$ cells per tube (about 0.5 mL beads).

Figure 6:
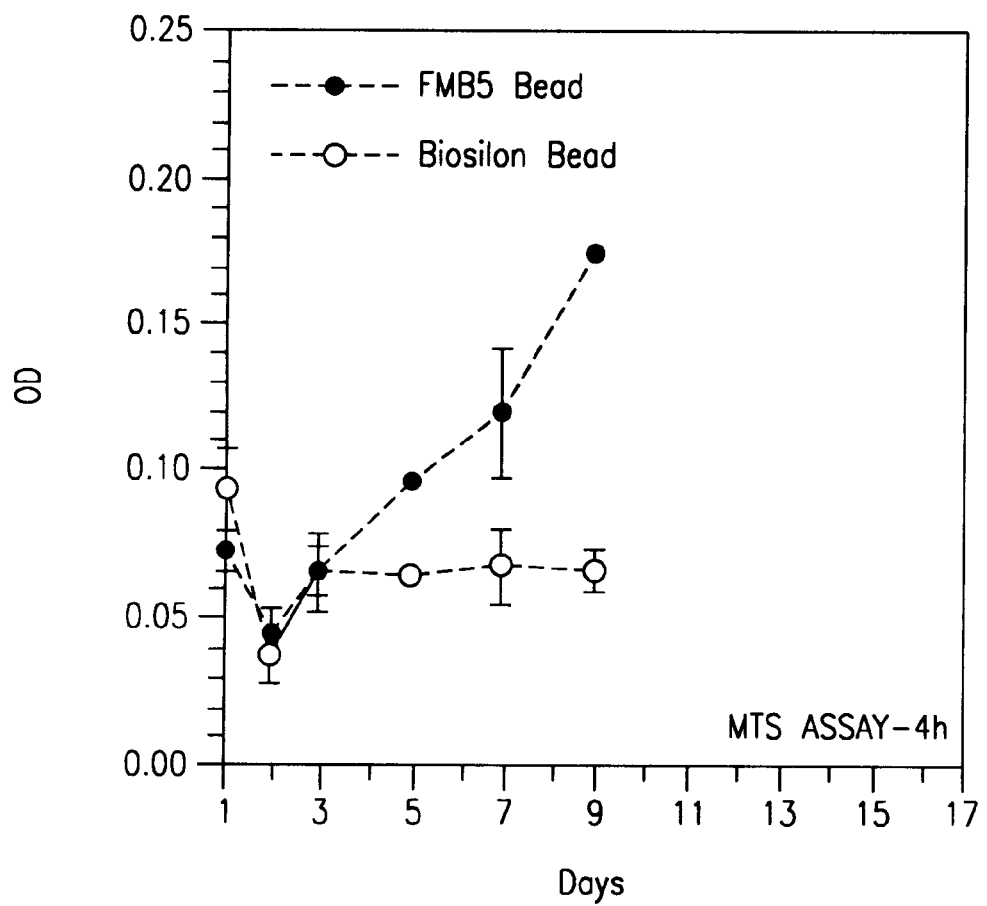
FIG. 6 represents a comparision of the growth of fibroblasts on FMB and Biosilon beads. Cell number was assayed by the MTS Assay.

In another experiment, the density of fibroblasts cultured with FMB was compared to the density of fibroblasts cultured with Biosilon micro-carrier beads (Biosilon, A/S NUNC, Foskilde, Denmark) using the MTS Assay (Berman, et al., *Biochimica et Biophysica Acta*, 1239:177–185 (1995)). In a direct comparison of fibroblasts grown on these two types of carriers, after 9 days in culture, cells on 0.37 g FMB in culture medium increased from $1.2 \times 10^5$ cells/mL to $4.8 \times 10^5$ cells (400% increase); those growing on 0.36 g Biosilon micro-carrier beads increased from $1.2 \times 10^5$ cells/mL to $1.8 \times 10^5$ cells/mL (50% increase) (see FIG. 6).

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A method for producing fibrin microbeads in the absence of glutaraldehyde as a cross linking agent, said method comprising the sequential steps of: (i) preparing an aqueous solution comprising fibrinogen, thrombin and Factor XIII; (ii) prior to the onset of coagulation, contacting said aqueous solution with an oil heated to a temperature of about 50–80° C. to form an emulsion; (iii) mixing the emulsion at a temperature of about 50–80° C. until fibrin microbeads comprising extensively cross-linked fibrin(ogen) are obtained; and (iv) isolating the fibrin microbeads.

2. The method of claim 1, wherein the aqueous solution comprising fibrinogen, thrombin and Factor XIII is prepared by contacting thrombin with purified fibrinogen containing endogenous Factor XIII.

3. The method of claim 1, wherein the aqueous solution comprising fibrinogen, thrombin and Factor XIII is prepared by combining thrombin with a cryoprecipitate containing endogenous fibrinogen and endogenous Factor XIII.

4. The method of claim 1, wherein the aqueous solution comprising fibrinogen, thrombin and Factor XIII is prepared by adding separate amounts of fibrinogen, Factor XIII and thrombin to an aqueous medium to form the aqueous solution.

5. The method of claim 1, wherein ratio of fibrinogen:thrombin:Factor XIII in the aqueous solution is 5–100 mg/mL:1–100 U/mL:1–50 U/mL.

6. The method of claim 1, wherein ratio of fibrinogen:thrombin:Factor XIII in the aqueous solution is 20–40 mg/mL:5–10 U/mL:2–20 U/mL.

7. The method of claim 1, wherein the aqueous solution further comprises at least one bioactive agent.

8. The method of claim 7, wherein the aqueous solution containing fibrinogen, Factor XIII and thrombin is contacted with the oil within about 30 seconds after preparing the aqueous solution.

9. The method of claim 1, wherein the oil is selected from the group consisting of vegetable oils, petroleum based oils, silicone oils, and combinations thereof.

10. The method of claim 9, wherein the oil is a vegetable oil selected from the group consisting of corn oil, olive oil, soy oil, coconut oil, and compinations thereof.

11. The method of claim 10, wherein the vegetable oil is corn oil.

12. The method of claim 1, wherein the oil is admixed with a hydrophobic organic solvent.

13. The method of claim 12, wherein the organic solvent is isooctane.

14. The method of claim 1, wherein the emulsion is mixed for about 3–9 hours.

15. The method of claim 1, wherein the fibrin microbeads are isolated by centrifugation, filtration, or a combination thereof.

16. The method of claim 1, which further comprises grading the isolated microbeads to the desired size.

* * * * *